United States Patent
Mace et al.

(10) Patent No.: US 7,803,538 B2
(45) Date of Patent: Sep. 28, 2010

(54) METHOD FOR DETECTING ALZHEIMER'S DISEASE

(75) Inventors: Sandrine Mace, Jouy-En-Josas (FR); Sylvain Ricard, Paris (FR); Emmanuelle Cousin, Paris (FR); Laurent Pradier, Verrieres (FR); Jésus Benavides, Chatenay Malabry (FR); Jean-François Deleuze, Comps la Ville (FR)

(73) Assignee: Aventis Pharma SA, Antony (FR)

( * ) Notice: Subject to any disclaimer, the term of this patent is extended or adjusted under 35 U.S.C. 154(b) by 497 days.

(21) Appl. No.: 10/869,977

(22) Filed: Jun. 17, 2004

(65) Prior Publication Data

US 2005/0003417 A1   Jan. 6, 2005

Related U.S. Application Data

(60) Provisional application No. 60/496,859, filed on Aug. 21, 2003.

(30) Foreign Application Priority Data

Jun. 20, 2003  (FR) .................................. 03 07501

(51) Int. Cl.
C12Q 1/68 (2006.01)
C12P 19/34 (2006.01)

(52) U.S. Cl. ..................... 435/6; 435/91.1; 435/91.2

(58) Field of Classification Search ............... None
See application file for complete search history.

(56) References Cited

U.S. PATENT DOCUMENTS 6,531,279 B1 *  3/2003  Blumenfeld et al. ........... 435/6

FOREIGN PATENT DOCUMENTS

| WO | WO00/15839 | * | 3/2000 |
|---|---|---|---|
| WO | WO 01/14414 | | 3/2001 |
| WO | WO 02/08424 | | 1/2002 |
| WO | WO 02/064781 | | 8/2002 |
| WO | WO 02/101392 | | 12/2002 |

OTHER PUBLICATIONS

NCBI SNP record Submitted SNP ss1342584, entered into dbSNP Sep. 6, 2000, pp. 1-3, printed from NCBI website Feb. 8, 2007.*
"Method Detail" entitled TSC-Sanger-19-26, printed Feb. 8, 2007 from http://www.ncbi.nlm.gov/SNP/snp_viewTable.cgi?mid=581, pp. 1-3.*
Hacker et al. Gut, 1997, vol. 40, pp. 623-627.*
Pennisi, Science, 281 (5384):1787-1789.*
Mace et al. Neurobiology of Disease, vol. 18, p. 119-125, 2005.*
Wollmer et al. American Journal of Medical Genetics Part B (Neurophychiatric Genetics) 141B:534-536 (2006).*
Minster et al. Neurobiol Aging (2008), doi: 10.1016/j.neurobiolaging.2008.01.006, pp. 1-2.*
Kaminski, Wolfgang E. et al., Complete Coding Sequence, Promoter Region, and Genomic Structure of the Human ABCA2 Gene and Evidence for Sterol-Dependent Regulation in Macrophages, Biochemical and Biophysical Research Communications, (2001), vol. 281, pp. 249-258.
Paleacu, Diana et al., Donepezil for the Treatment of Behavioral Symptoms in Patients With Alzheimer's Disease, Clinical Neuropharmacology, (2002), vol. 25, No. 6, pp. 313-317.
Vulevic, Bojana et al., Cloning and Characterization of Human Adenosine 5'-triphosphate-binding Cassette, Sub-family A, Transporter 2 (ABCA2), Cancer Research, (2001), vol. 61, pp. 3339-3347.
Wollmer, M. Axel et al., ABCA1 modulates CSF cholesterol levels and influences the age at onset of Alzheimer's disease, Neurobiology of Aging, (2003), vol. 24, pp. 421-426.
Homo Sapiens, NCBI.com, refSNP ID: rs908832.
Homo sapiens ATP-Binding cassette, sub-family A (ABC1), member 2 (ABCA2), transcript variant 1, mRNA, NCBI.com, Accession No. NM_001606.

* cited by examiner

*Primary Examiner*—Juliet C Switzer

(57) ABSTRACT

The present invention relates to a method for diagnosing an individual for early onset Alzheimer's disease by measuring the presence or absence of the minor allele of the rs908832 polymorphism of the ABCA2 gene. The presence of the minor allele of the rs908832 polymorphism of the ABCA2 gene indicates that the individual may be suffering from Alzheimer's disease or exhibits an increased risk of developing Alzheimer's disease.

7 Claims, No Drawings

METHOD FOR DETECTING ALZHEIMER'S DISEASE

The present invention relates to methods for the diagnosis or for the prognosis of Alzheimer's disease. It also relates to the kits for the diagnosis or for the prognosis of Alzheimer's disease.

Alzheimer's disease is a neurodegenerative disease which affects a large proportion of the elderly population. In clinical terms, this disease is characterized by a loss of cognitive functions and, in neuropathological terms, it is characterized by the presence in the brain of intracellular neurofibrillar deposits and of extracellular deposits of the β-amyloid (Aβ) peptide forming amyloid plaques. Amyloid plaques are mainly composed of Aβ peptides containing 40 or 42 amino acids, which are generated by a process of proteolysis of the β-amyloid peptide precursor protein (APP). Extracellular deposits of Aβ are specific for Alzheimer's disease. They represent the early and invariable characteristic of all forms of Alzheimer's disease, including the familial forms.

The familial forms of the disease appear relatively early (between 40 and 60 years old). They appear to be due, at least in part, to mutations in the APP gene and in the presenilin-1 (PS1) and presenilin-2 (PS2) genes. Mutations in these three genes induce changes in the proteolysis of APP, leading to an overproduction of Aβ and to the early appearance of the pathology and of the symptoms, which are similar to those of the sporadic forms of Alzheimer's disease.

A connection between cholesterol and Alzheimer's disease has also been established from epidemiological studies and from results of recent biochemical and cell biology studies (see review Hartmann, T. (2001) *TINS* 24: S45-48). A high cholesterol level at adult age, and also a high arterial blood pressure, significantly increase the risk of Alzheimer's disease (Kivipelto et al., 2001 *Br Med J.* 322: 1447).

On the other hand, a very reduced risk is recorded in populations being treated with cholesterol-lowering agents of the statin type (Wolozin et al. (2000) *Arch Neurol.* 57: 1439; Jick et al. (2000) *Lancet* 356: 1627).

The molecular link appears to have been recently established. In vitro and in vivo, a high cholesterol level increases production of the Aβ peptide and accelerates the appearance of amyloid plaques (Sparks et al. (1994) *Exp. Neurol.* 126: 88-94; Refolo et al. (2000) *Neurobiol. Dis.* 7: 321-331; Puglielli et al. (2001) *Nat. Cell Biol.* 3: 905; Shie et al. (2002). *Neuroreport* 13: 455), whereas inhibitors of the pathway for cholesterol synthesis decrease them (Simons et al. (1998) *PNAS USA* 95: 6460-6464; Fassbender et al. (2001) *PNAS USA* 98: 5856, Refolo et al., (2001) *Neurobiol. Dis.* 8: 890-899).

Despite significant advances, the medical community is still confronted with a lack of molecules which are really effective against Alzheimer's disease. One of the reasons for this lack of molecules lies in the difficulty in finding targets for effective screening of molecules capable of exerting a therapeutic action against this disease.

Furthermore, early detection of this disease appears to be determinant, in order to provide treatment before the first symptoms, which are highly disabling to the patients, begin to manifest themselves.

In addition, due to the varied forms of this disease, it appears to be necessary to target the treatment as a function, firstly, of the individuals to be treated and, secondly, of the molecule which can be used for the treatment. This pharmacogenomic or pharmacogenetic approach appears to be increasingly important.

The ABCA2 protein is a protein belonging to the large family of ABC (ATP-binding cassette) type cholesterol transporters. This transporter is expressed specifically in the brain.

The cloning of the ABCA2 gene was described in 2000 by Zhao et al. (Biochem. J., 350, 865-872). The sequence was also the subject of PCT application WO 01/14414, deposited by the company ACTIVEPASS PHARMACEUTICALS. Various hypotheses are put forward in that application, regarding the role of ABCA2, but without there being any result to support them.

Various polymorphisms of the ABCA2 gene have already been identified. Their sequences are in particular accessible in the dbSNP database of the NCBI. Among the various polymorphisms listed in this base, the polymorphism rs908832 is described.

This polymorphism is characterized by a major allele in the Caucasian population, which is a guanine located at position 348 on the sequence SEQ ID No. 2, and aminor allele in the Caucasian population, which is an adenine located at position 348 on the sequence SEQ ID No. 1.

Alternatively, this single nucleotide polymorphism is represented by the sequences SEQ ID No. 3 and SEQ ID No. 4 which are partially complementary to SEQ ID No. 1 and SEQ ID No. 2, respectively. This polymorphism is then characterized by a major allele in the Caucasian population, which is a cytosine located in position 201 on the sequence SEQ ID No. 4, and aminor allele in the Caucasian population, which is a thymidine located at position 201 on the sequence SEQ ID No. 3.

This polymorphism is synonymous, i.e. it does not modify the sequence of the translated protein. The two alleles of the polymorphism are part of codons which encode an aspartic acid. This coding polymorphism is located on exon 14 of the transcript exhibiting the sequence SEQ ID No. 5 at position 2185.

Surprisingly, the applicant has shown that individuals exhibiting the minor allele of the rs908832 polymorphism of the ABCA2 gene have an increased risk of early development of Alzheimer's disease.

This discovery is particularly important since it provides, to the applicant's knowledge, for the first time, proof of a link between the ABCA2 protein, and in particular a polymorphism of the gene encoding this protein, and a pathological state, such as Alzheimer's disease.

It makes it possible to confirm and/or to give a prognosis for the severity of the affliction in patients for whom Alzheimer's disease has already been diagnosed, and also the probable effectiveness of the treatments envisioned, or else to give a prognosis for the risks of appearance of the disease in individuals not exhibiting symptoms of Alzheimer's disease, including individuals related to patients for whom the diagnosis has been confirmed.

It also makes it possible to confirm a major functional role for ABCA2 in the physiopathology of Alzheimer's disease, justifying the use of tests to screen for molecules capable of exerting a stimulatory or inhibitory action on the activity of ABCA2 for the purpose of a therapeutic application against Alzheimer's disease.

A first subject of the present invention is thus a method for the diagnosis or for the prognosis of Alzheimer's disease in an individual. Said method comprises at least one step of detection of the alleles of a polymorphism of the ABCA2 gene. Advantageously, such a polymorphism is a polymorphism involved in Alzheimer's disease. It is preferably the rs908832 polymorphism, but it may be any other polymorphism in genetic linkage disequilibrium with the rs908832 polymorphism.

Suitable individuals may, for example, be:
- individuals who do not exhibit the symptoms of Alzheimer's disease,
- individuals in whom the risk of developing Alzheimer's disease has already been detected, but who do not yet exhibit the symptoms of the disease, and
- individuals who have previously been diagnosed as suffering from Alzheimer's disease, for whom a confirmation of the diagnosis is desired.

The step or steps of detection (which may or may not be simultaneous) of the presence or absence of the minor allele of the rs908832 polymorphism are carried out directly or indirectly by any suitable means using biological samples.

The present invention therefore also relates to a method for screening biological samples taken from individuals, in particular individuals not exhibiting symptoms of Alzheimer's disease, in order to detect individuals highly liable to develop Alzheimer's disease. Such a screening comprises searching, possibly simultaneously, in said biological samples, for the presence of the minor allele of the rs908832 polymorphism.

Said samples containing the DNAs or the proteins to be identified may be of various origin. They may, for example, be blood samples, sperm samples or hair samples (with the roots) or any other sample containing nucleated cells. Preferably, the biological samples analyzed are blood samples. In this case, the DNA to be identified is taken from the leukocytes.

For the purpose of the present invention, the term "biological sample" is intended to mean samples directly derived from the individual for whom a diagnosis or a prognosis is desired without any other transformation, or samples which have undergone one or more steps of preparation so as to conserve only a fraction thereof which is of use for the detection steps, for example a crude cell extract.

The techniques for detecting or identifying the presence or absence of the DNAs carrying the minor allele of the rs908832 polymorphism can be combinations of the techniques of Polymerase Chain Reaction (PCR), of hybridization, of Southern blotting, of digestion with nucleases, of Restriction Fragment Length Polymorphism (RFLP) and/or of direct sequencing of the PCR products. All these techniques are known to those skilled in the art.

In general, all the techniques for identifying the DNAs carrying the minor allele of the rs908832 polymorphism which can be used in the context of the present invention comprise a prior step of collecting the biological sample(s) containing the DNAs to be identified and a step of extraction of the genomic DNA according to the standard techniques well known to those skilled in the art, for example according to the method of Smith et al. (*The Lancet*, 1992, 339, pp. 1375-7).

Such a method of identification can comprise:
a) extracting the DNA of said individual,
b) amplifying said isolated DNA using primers capable of amplifying the sequences corresponding to each one of the alleles of the rs908832 polymorphism of the ABCA2 gene, and
c) determining at least one of the alleles of the rs908832 polymorphism of the ABCA2 gene in the amplified DNA.

According to an advantageous embodiment, the PCR technique is used. Thus, step b) advantageously comprises a polymerase chain reaction step. This technique consists first of all in synthesizing oligonucleotides complementary to the sequence of the regions which delimit the DNA segment to be amplified (primers). These oligonucleotides serve as primers for the DNA polymerase. Then, the steps of heat-denaturation (92-95° C.), in order to separate the two DNA strands, of hybridization with the two specific primers by virtue of a decrease in temperature (50-55° C.) and of extension of the primers with a DNA polymerase at 70-72° C. are carried out.

Such primers for amplifying each one of the alleles of the rs908832 polymorphism of the ABCA2 gene, and in particular of the minor allele, and also the sequences complementary thereto, constitute other subjects of the present application. Advantageously, they have respective sequences such that the number of bases between their respective points of hybridization on the DNA molecule is between 25 and 2500 base pairs, and preferably between 100 and 500 base pairs.

Advantageously, such primers have between approximately 15 and 30 contiguous nucleotides of the sequence SEQ ID No. 3 or of the sequence SEQ ID No. 4. Preferably, they are a pair of primers having the sequences SEQ ID No. 6 and SEQ ID No. 7.

According to an advantageous embodiment, a subject of the present application is a method wherein the amplified DNA carrying the minor allele of the rs908832 polymorphism is distinguished from the amplified DNA not carrying this allele by specific hybridization of two probes, each one of them being specific for one of the two forms of the polymorphism. These probes, and also the sequences complementary thereto, constitute other subjects of the present application.

Advantageously, these probes consist respectively of approximately 12 to 17 contiguous nucleotides of the sequence SEQ ID No. 3 or SEQ ID No. 4. Preferably, they have the sequences SEQ ID No. 8 and SEQ ID No. 9, respectively.

The amplified DNA carrying the minor allele of the rs908832 polymorphism can also be distinguished from the amplified DNA not carrying this allele by the technique using the 5' nuclease activity of DNA polymerase I (TAQMAN® chemical reagent for use in polymerase chain reaction analysis).

According to an advantageous embodiment, a subject of the present application is a method wherein the amplified DNA carrying the rs908832 polymorphism is distinguished from the amplified DNA not carrying this polymorphism by restriction fragment polymorphism (RFLP) analysis. Advantageously, the restriction fragments have been obtained by digestion of the amplified DNA with a restriction enzyme before migration in agarose gel, Southern blotting onto membrane and hybridization.

In order to obtain both greater sensitivity and better specificity, it is also possible to carry out two successive PCRs using two different pairs of primers ("nested PCR"): a first pair of external primers which makes it possible to obtain an amplified DNA fragment as in conventional PCR and a second pair of internal primers in order to amplify the DNA fragment obtained from the first PCR.

In order to determine the genetic footprint of the desired region, the DNA fragments obtained by PCR can also be separated by electrophoresis according to their size and visualized with ETB (ethidium bromide) and ultraviolet rays.

A particularly advantageous possibility in the present case consists in carrying out a PCR with a first primer having at its 3' end the mutated nucleotide sequence, and a second primer having at its 3' end the wild-type nucleotide sequence. The difference in denaturation temperature in these two cases, and consequently in efficiency of amplification, makes it possible to distinguish the mutant DNA from the wild-type DNA.

According to another alternative, the amplified DNA fragments are directly identified by dot blot technique, which consists in depositing a sample of the DNA fragments produced from the PCR onto a nylon filter, in denaturing the DNA fragments, in hybridizing them with a radioactive specific probe and in washing in order to eliminate the excess radioactive product not attached, and then in performing an autoradiogram. The revealing can also be carried out by other means, using specific probes comprising a label other than a radioactive label, for example a dye or else a fluorescent label.

According to another alternative, it is also possible to detect the presence or absence of mutations in the DNAs comprising the rs908832 polymorphism by direct sequencing of all or part of the amplified DNA fragments. Such a method consists in determining the nucleotide sequence at the rs908832 polymorphism. The sequencing can be carried out by any method known to those skilled in the art, for example by the Sanger method or else by the Maxam and Gilbert method.

According to another alternative, the detection of the presence or absence of the DNAs carrying the rs908832 polymorphism can be carried out using the Southern blotting technique, which consists in performing an electrophoresis of the DNA fragments obtained after treatment with one or more restriction enzymes. The gel is then denatured and blotting is carried out onto a nylon membrane. This membrane is intended to be hybridized with a specific probe. After washing to eliminate the excess radioactive product not attached, the film is applied to the membrane. One or more bands corresponding to the DNA fragments recognized by the probe can thus be detected.

It is also possible to use the RFLP technique combined with the Southern blotting and/or PCR technique to detect the presence or absence of the rs908832 polymorphism. RFLP makes it possible to compare the DNAs of various individuals and to investigate whether point mutations causing restriction sites to appear or disappear have occurred. Two DNAs of identical sequence treated with restriction enzymes will give identical fragments, and the Southern blots obtained with these fragments will therefore be identical. On the other hand, if a restriction site has disappeared, or alternatively has appeared, subsequent to a mutation, the fragments will no longer have identical sizes and this will be visible on the autoradiograms. The same is true if a novel restriction site has appeared subsequent to a mutation.

It is also possible to detect the rs908832 polymorphism of the ABCA2 gene by determining the nucleotide at position 2185 of the transcript encoding the ABCA2 protein.

All the techniques described above are well known to those skilled in the art. Any other technique which is known and also suitable for detecting the presence or absence of the rs908832 polymorphism can be used. In this respect, mention may, for example, be made of the techniques of Ligase Chain Reaction, Strand Displacement Amplification, Transcription-based Amplification, etc. Advantageously, said detection steps are carried out by PCR, RFLP, Southern blotting and/or a combination of these techniques, in accordance with the methods described in the literature (see, for example: Gough et al., *Nature,* 1990, 347, p.773; Kagimoto et al., *J. Biol. Chem.,* 1990, 265, p. 17209; Wolf et al., *The Lancet,* 1990, 336, p. 1452; Hayashi et al., *Nucleic Acids Res.,* 1991, 19, p. 4797; Daly et al., *Pharmacogenetics,* 1991, 1, p. 33; Spurr et al., *Methods Enzymol.,* 1991, 206, p. 149; Armstrong et al., *The Lancet,* 1992, 339, p. 1017; Kurth et al., *Am. J. of Med. Genet.,* 1993, 48, p. 166; McCann et al., *J. Neurol. Sci.,* 1997, 153, p. 50; Stroombergen et al., *Hum. & Exper. Toxicol.,* 1999, 18, p. 141).

All these methods of detection are particularly useful since they constitute the basis for determining whether an individual may be suffering from Alzheimer's disease or else exhibits an increased risk of developing Alzheimer's disease.

Thus, another subject of the present invention concerns a method for analyzing biological samples taken from an individual, which consists in:
 a) determining the genotype for the ABCA2 gene of said individual, and
 b) converting the data obtained in a) in order to give a prognosis for said individual's risk of developing Alzheimer's disease and the effectiveness of therapeutic treatments which can be envisioned for this disease.

According to another aspect, the present invention also relates to the sets, or kits, for the diagnosis or for the prognosis of Alzheimer's disease in an individual.

Such kits can be in the form of a packaging, compartmentalized so as to accept various containers, such as, for example, vials or tubes. Each one of these containers comprises the various elements required to carry out the detection of the presence or absence of the DNA carrying the rs908832 polymorphism.

Said elements for carrying out the detection reaction(s) are chosen from those described above. They may be, for example:
 a pair of primers which hybridize with a defined region of the ABCA2 gene and, optionally, the means necessary for carrying out an amplification reaction, or
 oligonucleotide probes, optionally immobilized on a support and comprising a detectable label, and, optionally, the reagents necessary for carrying out a hybridization reaction.

Another subject of the present invention is a method for treating Alzheimer's disease, which comprises:
 at least one step of detection of the presence of the minor allele of the rs908832 polymorphism in an individual, and
 the administration of a compound or of a mixture of compounds known for their activity against Alzheimer's disease to an individual exhibiting the minor allele of the rs908832 polymorphism.

Preferably, the disease is early Alzheimer's disease.

Another subject of the present invention is a method for selecting a compound intended to be administered to an individual exhibiting a disease associated with the minor allele of the rs908832 polymorphism of the ABCA2 gene which comprises:
 a. at least one step of determination of the presence of the minor allele of the rs908832 polymorphism of the ABCA2 gene in a biological sample from said individual, and
 b. the selection of the appropriate compound if said allele is present.

Another subject of the present invention is a method for selecting a compound intended to be administered to an individual exhibiting Alzheimer's disease, which comprises:
 a. at least one step of determination of the presence of the minor allele of the rs908832 polymorphism of the ABCA2 gene in a biological sample from said individual; and
 b. the selection of the appropriate compound if said allele is present.

The present application also relates to the use of a compound or of a mixture of compounds known for their activity against Alzheimer's disease, for producing a medicinal product for the treatment of an individual suffering from Alzheimer's disease, in whom the presence of the minor allele of the rs908832 polymorphism has been detected prior to the treatment.

Said compounds known for their activity against Alzheimer's disease may, for example, be acetylcholine esterase inhibitors (AchEIs such as Donepezil (Aricept), Galantamine (Reminyl) or Exelon (rivastigmine)), NMDA receptor channel antagonists (such as Memantine (Ebixa)), inhibitors of amyloid peptide production, such as BMS 299897, or future ABCA2-activity modulators.

The compounds of the combination can be administered orally, parentally, transdermally or rectally, either simultaneously or separately, or in a manner spread out over time.

The compounds are formulated in the form of pharmaceutical compositions containing the combination of one or more compounds as defined above with a pharmaceutically acceptable vehicle.

As solid compositions for oral administration, use may be made of tablets, pills, powders (gelatin capsules, cachets) or granules. In these compositions, the active principles are mixed with one or more inert diluents, such as starch, cellulose, sucrose, lactose or silica, under a stream of argon. These compositions can also comprise substances other than the diluents, for example one or more lubricants such as magnesium stearate or talc, a dye, a coating (sugar-coated tablets) or a varnish.

As liquid compositions for oral administration, use may be made of solutions, suspensions, emulsions, syrups and elixirs, which are pharmaceutically acceptable, containing inert diluents such as water, ethanol, glycerol, plant oils or paraffin oil. These compositions can comprise substances other than the diluents, for example wetting, sweetening, thickening, flavoring or stabilizing products.

The sterile compositions for parental administration can preferably be aqueous or nonaqueous solutions, suspensions or emulsions. As solvent or vehicle, use may be made of water, propylene glycol, a polyethylene glycol, plant oils, in particular olive oil, injectable organic esters, for example ethyl oleate, or other suitable organic solvents. These compositions can also contain adjuvants, in particular wetting agents, isotonicity agents, emulsifiers, dispersing agents and stabilizers. The sterilization can be carried out in several ways, for example by aseptic filtration, by incorporating sterilizing agents into the composition, by irradiation or by heating. They can also be prepared in the form of sterile solid compositions which may be dissolved at the time of use in sterile water or any other injectable sterile medium.

The compositions for rectal administration are suppositories or rectal capsules which contain, besides the active product, excipients such as cocoa butter, semisynthetic glycerides or polyethylene glycols.

The pharmaceutical compositions containing the combination as defined above generally contain 0.1 to 500 mg of compound.

The doses depend on the desired effect, on the duration of the treatment and on the route of administration used; they are generally from 0.1 to 500 mg of compound per day, orally, for an adult.

In general, the physician will determine the appropriate dosage as a function of age and weight and of all the other factors specific to the individual to be treated.

The present invention also relates to a transgenic animal into the genome of which is inserted at least one exogenous DNA sequence carrying the minor allele of the rs908832 polymorphism such that the function of the ABCA2 gene is modified.

The term "transgenic animal" is intended to mean any nonhuman animal exhibiting an artificial modification of its genome. The modification of the genome can be the result of an alteration or of a modification of one or more genes by "knock-in" or by "knock-out" (inactivation/modification of genes by homologous recombination), or the overexpression of the human gene under the control of promoters specific for neuronal cell types (such as Thyl, PDGF or prion) or glial cell types (such as GFAP) in mice. This modification can be due to the action of conventional altering or mutagenic agents or else can be brought about by stable insertion of an expression cassette allowing expression of a hybrid gene. In particular, it is for example possible to carry out the procedures according to methods identical or similar to those described in applications WO 01/02552 or else WO 01/13176.

The modification of the genome can also be the result of an insertion of (a) gene(s) or of a replacement of (a) gene(s) in its (their) wild-type or mutated form.

The modifications are advantageously carried out on reproductive stem cells.

At the current time, modification of the genome using "knock-in" and "knock-out" technology is limited to mice as a model due to the fact that only stem cells (termed "ES" cells) having the ability to colonize the germinal line derived from the mouse embryo are available. When ES cell lines are available for other species, it will be possible for those skilled in the art to readily apply these technologies to these other species in order to generate KO and/or KI models. In addition, approaches based on the use of oligonucleotides (DNA, RNA or hybrids), alone or associated with DNA/RNA-modifying enzymes, can be used to introduce a defined modification/mutation at a given locus in the genome. Even irradiation or chemical mutagens which induce random modifications in the genome can be used if they are combined with an effective set of biological markers (phenotype) and with a high throughput positional cloning procedure.

The most direct approach for modifying the genome of laboratory animals (mice, rats, cows, pigs, sheep, etc.) is, however, the random integration of transgenes by microinjection of linearized DNA into one or two pronuclei of oocytes fertilized at the single-cell stage (preferably, to avoid generating chimeric animals, although injection at the stage of two or more cells may also be used). As a general rule, a transgene is made up of two parts: the regulatory elements which impose the spatio-temporal control of expression of the RNA encoded by the DNA, and said juxtaposed DNA (cDNA or genomic fragment). These two elements (the regulatory element and the DNA encoding the desired protein) can be homologous or else heterologous to the target genome. The transgenic animals concerned are generally chosen from non-human mammals. They may, for example, be murine, i.e. mice, rats and guinea pigs, rabbits, cats, dogs, ovines or else bovines. Preferably, they are murine animals, rats or rabbits obtained according to conventional transgenesis techniques. Other subjects of the present invention are stem cell lines and cell lines differentiated from these stem cell lines, into the genome of which is inserted at least one exogenous genomic DNA sequence carrying the minor allele of the rs908832 polymorphism.

Succinctly, the production of the transgenic animals, of the stem cell lines and of the differentiated cell lines according to the invention consists of a method using the generation of transgenic animals by insertion, by homologous recombination, of an exogenous genomic DNA encoding the ABCA2 protein into the corresponding gene of the animal (the insertion of the transgene is targeted immediately after the promoter of the animal's gene so as to impose the correct expression profile on the transgene and to prevent expression of the animal's endogenous gene: knocked out) or else by insertion of the specific mutation described in the present invention, corresponding to an isoform of the human ABCA2 gene, into the animal's endogenous gene (the modification is brought about by homologous recombination in stem cells: knocked in), or else by overexpression of the ABCA2 gene carrying the minor allele of the rs908832 polymorphism.

In the case of mice, these animals may advantageously be crossed with transgenic mice carrying the human APP gene bearing Alzheimer-type mutations and which develop amyloid plaques. The double transgenic animals thus obtained reproduce the genotype observed in patients suffering from Alzheimer's disease or at risk. The rs908832 polymorphism genotype of the new born animal thus obtained can be controlled using the techniques already described above, in particular using an amplification reaction (PCR) and/or Southern blotting.

Such transgenic animals are particularly valuable since they provide an advantageous model for understanding Alzheimer's disease, which very faithfully reproduces the characteristics of Alzheimer's disease. By comparison with known models, this model makes it possible in particular to demonstrate compounds which are particularly suitable for the treatment of Alzheimer's disease, in particular as described in humans. These compounds may be chemical molecules, peptide or protein molecules, antibodies, chimeric molecules and also antisense DNAs or ribozymes.

The compounds thus demonstrated can be used as a medicinal product, as they stand or in combination with a pharmaceutically acceptable vehicle, in order to obtain a pharmaceutical composition. They may in particular be sterile, isotonic, saline solutions (monosodium or disodium phosphate, sodium, potassium, calcium or magnesium chloride, etc., or mixtures of such salts), or dry, in particular lyophilized, compositions which, when sterilized water or physiological saline, as appropriate, is added to them make it possible to constitute injectable solutes. The injections can be carried out stereotaxically, topically, orally, parenterally, intranasally, intravenously, intramuscularly, subcutaneously, intraoccularly, transdermally, etc.

Demonstration of the compounds described above is based on bringing the animal model of the invention into contact, in particular by administration such as for example an injection, with a compound or a mixture of compounds supposed to have an action, and then measuring the effect(s) of the compounds, in particular within the brain in the model, on various biochemical and/or histological changes.

Besides the fact of being able to test, in vivo, therapeutic compounds for preventing, attenuating or curing Alzheimer's disease, these transgenic animals also make it possible to have an animal model for Alzheimer's disease which is of use for screening environmental factors which induce or accelerate the pathogenesis, or else for studying behavior during development of the disease and studying the various biological mechanisms which are involved, for example with the aim of studying new medicinal products or determining the effective amounts of medicinal products and the toxicity. Thus, another subject of the present invention concerns the use of a transgenic animal, of stem cell lines or of differentiating cell lines as defined above, for testing the activity of compounds or of methods intended to prevent and/or treat Alzheimer's disease. Another subject of the invention concerns a cell extracted from the transgenic animals as described above, and also its use for demonstrating compounds intended for the treatment of Alzheimer's disease.

The demonstration of compounds described above is based on bringing cells extracted from the animal model of the invention into contact with a compound or a mixture of compounds supposed to have an action, and then measuring the effect(s) of the compounds on whole cells, in cell homogenates or on a subcellular fraction, on various parameters such as cell death for example.

Besides the above arrangements, the present invention also comprises other characteristics and advantages which will emerge from the examples and figures which follow, and which should be considered to illustrate the invention without limiting the scope thereof.

EXAMPLES

Example 1

Study of the Genotype of the rs908832 Polymorphism of the ABCA2 Gene in a Patient Sample A collection of DNAs derived from patients of Caucasian origin suffering from Alzheimer's disease and from control individuals was used, after they had given their informed consent.

The frequency of the polymorphisms was determined by genotyping a sample of 47 individuals of a panel marketed by the Coriell Institute (USA).

Ten polymorphisms (including the rs908832 polymorphism) were selected on the basis of their location in the gene and of their frequency in order to be genotyped in the patients suffering from Alzheimer's disease and the controls.

The genotypes were prepared by the 5' nuclease assay method (technique for allelic discrimination from Applied Biosystems, Foster City, USA), and then a Chi2 statistical analysis was carried out by testing the association of each one of these markers with Alzheimer's disease (heterogeneity test). For the analysis, groups were distinguished according to the age at which the disease appeared early (before or at 65 years old) or late (after 65 years old)) and its origin (sporadic (first known case) or familial (other cases already known in the same family)).

The results obtained for the rs908832 polymorphism are as follows:

frequency of the minor allele (T) in the patients (440 genotypes): 7.4 frequency of the minor allele (T) in the controls (519 genotypes): 3.4

The Hardy-Weinberg proportions were verified in the patients and the controls: no significant deviation is observed, which confirms that there is no genotyping error.

Results of the tests carried out in the patients exhibiting an early form of the disease (before or at 65 years old):

136 sporadic cases vs 272 controls:

heterogeneity test: chi2 (1ddl)=22.69 p=$2 \times 10^{-6}$ allelic test (freq(T) vs freq(C)): chi2 (1ddl)=21.27 p=$4 \times 10^{-6}$ 104 familial cases vs 272 controls:

heterogeneity test: chi2 (2ddl)=7.80 p=0.02 allelic test (freq(T) vs freq(C)): chi2 (1ddl)=7.27 p=$7 \times 10^{-3}$

The odd ratio was estimated by logistic regression in the 240 patients exhibiting the early form (adjustment with respect to the sex and APOE-e4 status). The result is also significant: OR=3.97 IC=[2.23–7.09].

The values obtained remain significant (threshold fixed at 0.05) even after correction for multiple tests by the Bonferroni method.

These results indicate that the ABCA2 gene is a gene which is important in the etiology of Alzheimer's disease.

In terms of risk, this result is of the same order of magnitude as the risk conferred by the apolipoprotein E4, the most commonly known risk factor for Alzheimer's disease to date.

Example 2

Production of Transgenic Mice

1. Generation of a Transgenic Mouse Expressing the Human ABCA2 Protein

Mutagenesis of the human ABCA2 protein is carried out using an in vitro mutagenesis system such as Sculptor™ (Amersham, France). The coding region of ABCA2 is subcloned into a cloning vector of the Bluescript type (stratagene) and the mutations are introduced according to the protocol provided by the manufacturer, using oligonucleotides containing the desired mutation. The mutated sequences are to be verified by sequence analysis.

2. Generation and Identification of the ABCA2 Transgenic Mice

To construct the transgene, the genomic DNA encoding ABCA2 and exhibiting the minor allele of the human rs908832 polymorphism is subcloned into the polylinker of a vector for transgenic expression specific for certain tissues/cell types, such as THYI (Lüthi et al., J. Neuroscience, 17, pp. 4688-99), PDGF or prion for neuronal types, or GFAP for astrocytic types. A plasmid preparation kit (Qiagen) is used to prepare the supercoiled DNA. For the microinjection, the vector sequences have to be eliminated by digestion with a defined restriction enzyme, leaving intact the entire transgene and separating it from the needless sequences of the cloning vector. The fragment containing the expression cassette is then purified by agarose gel electrophoresis.

The aliquots intended for the microinjection are dialyzed against a TE buffer (10 mM Tris pH 7.4; 0.1 mM EDTA) on a floating filter (Millipore; membrane type: VS; 0.025 µm) and then filtered (Spin-X; Costar; polyacetate membrane; 0.22 µm). The DNA is diluted to the final concentration of 1-2 ng/µl for the microinjection. The purified fragment is injected into one of the two pronuclei of the fertilized mouse oocytes. The surviving embryos are immediately transplanted into the oviduct of ("pseudopregnant") adoptive mothers. The presence of the transgene in the newborns is determined either by PCR or by Southern analysis, using specific probes/sequences. By virtue of all these analyses, it is possible to exclude any major rearrangement or deletions of the transgene in the founders and their descendants.

3. Generation of Transgenic Animals Comprising the Human ABCA2 Protein in their Genome Homologous recombination technology in stem cells is used to introduce the ABCA2 gene exhibiting the minor allele of the human rs908832 polymorphism into the mouse gene, at the desired predefined position. The primers and samples described in the present invention can be readily used to screen isogenic mouse genomic libraries (lambda, BAC, YAC, etc. libraries) in order to isolate and clone the corresponding mouse gene. Said mouse gene is characterized in terms of its genomic organization and its sequence using standard techniques known to those skilled in the art (restriction site mapping, sequencing, bioanalytical tools) in order to define the exact site where the human DNA should be inserted to obtain the desired expression profile for the human DNA while at the same time definitively interrupting the expression of the murine gene. Once the exact position has been identified, a standard targeting vector for stem cells (i.e. a vector having markers for selection of the desired events, said markers all being well known to those skilled in the art specialized in the field) is constructed. Rapidly, a selection cassette (gene for resistance to an antibiotic) is placed at the limit of the 3' and 5' ends of the mouse genomic DNA fragments (2-6 kb) identical to the 3' and 5' extensions of the sequence of the murine ABCA2 gene located immediately after the selected site of insertion.

Based on knowledge of the mouse gene, a positive control vector for screening of the recombinant stem cells is generated (the vector reproduces the locus of the murine gene once integration has successfully taken place) in order to optimize and validate the high throughput screening procedure.

The DNA is purified for the targeting experiments in accordance with standard procedures. The targeting vector is introduced into the stem cells using standardized electroporation techniques, after which the stem cell clones are subjected to a sequential screening procedure (antibiotics) so as to promote the clones of stem cells carrying the desired recombination. In general, the screening takes approximately 2 weeks. The resistant stem cell clones are screened by PCR and/or Southern.

The clones of stem cells having the desired recombination without any other detectable modification in their genome are developed so as to obtain sufficient cells. Said cells are then injected into 3 and a half-day embryos obtained from a female having ovulated naturally. The surviving blastocytes (comprising the stem cells) are implanted into a recipient female, which will allow the blastocytes to develop to term and will give birth to newborn young mice made up of cells originating from the host blastocytes and the stem cell clones. This type of animal is referred to as a "chimeric animal".

These chimeras (preferably males since most of the stem cell lines are obtained from male mice) are "matched" with wild-type mice so as to obtain animals which are heterozygous for the modification. Breeding heterozygous animals with one another makes it possible to generate homozygous animals.

4. Generation of Transgenic Animals Comprising the Minor Allele of the rs908832 Polymorphism of the Human ABCA2 Gene in their Corresponding Gene The murine gene is isolated and characterized in the same way as described above. For this type of modification, it is essential to compare the human gene and the murine gene in order to identify the exact position where the point of mutation found in humans must be introduced into the murine gene. A bioanalysis is essential at this stage. At the end, the targeting vector is developed and assembled in the same way as described above. After successful homologous recombination, nothing more than the desired point of mutation has changed in the coding sequence of the murine gene. Some selection markers can remain in an intron, but they generally have no effect on expression of the gene. If necessary, they can be removed using a second generation of targeting vectors which include recombinase recognition elements. Once the construct has been assembled, the steps are identical to those of the procedure described above.

In general, these ABCA2 transgenic mice will be favorably crossed with transgenic mice expressing the APP gene carrying the mutations of the familial forms of Alzheimer's disease in order to promote the deposition of amyloid plaques.

5. Neurohistopathology

Preparation of Brain Tissue

The mice must be deeply anaesthetized (Pentobarbital: 60 mg/ml/kg i.p., Ketamine: 40 mg/ml/kg i.p.) and then perfused transcardially with physiological saline and then paraformaldehyde (4% in PBS). Next, the brains are removed and then post-fixed in the same fixing solution for 24 hours at 4° C. After fixing, the brains are separated into right and left half-brains and then subjected to the standard protocol for paraffin embedding.

The paraffin-embedded left half-brains of the transgenic and nontransgenic mice, and also blocks of postmortem human brain tissue (frontal cortex) from individuals suffering from Alzheimer's disease and from a control individual, are sectioned at a thickness of 6 μm (serial sections), using a microtome (LEICA RM 2155, France). The tissue blocks corresponding to the right half-brains of the transgenic and nontransgenic mice are sectioned at a thickness of 25 μm Immunoreactivity for the Aβ amyloid peptide will be detected as commonly described by those skilled in the art.

The invention claimed is:

1. A method for determining whether a Caucasian individual may have an increased risk of early development of Alzheimer's disease, comprising the steps of:
   i. obtaining a biological sample of the Caucasian individual that contains DNA from the Caucasian individual; and
   ii. determining whether the DNA of the biological sample contains a minor allele rs908832 polymorphism of the ABCA2 gene in which an adenine is located at position 348 of SEQ ID NO:1, or a thymidine is located at position 201 of SEQ ID NO:3 wherein the presence the minor allele rs908832 polymorphism of the ABCA2 gene indicates the Caucasian individual may have an increased risk of early development of Alzheimer's disease.

2. The method according to claim 1, wherein said biological sample contains nucleated cells.

3. The method according to claim 2 wherein said biological sample is selected from the group consisting of blood, sperm and hair.

4. The method according to claim 1, wherein the determining step is carried out by techniques selected from the group consisting of polymerase chain reaction (PCR), hybridization, Southern blotting onto membrane, digestion with nucleases, restriction fragment length polymorphism (RFLP), and direct sequencing.

5. The method according to claim 4, wherein the determining step is carried out using the polymerase chain reaction in which DNA of the biological sample is amplified, wherein the presence of the minor allele rs908832 polymorphism of the ABCA2 gene in the amplified DNA is determined by a technique using the 5' nuclease activity of DNA polymerase I.

6. The method according to claim 5 wherein said amplified DNA carrying the minor allele rs908832 polymorphism of the ABCA2 gene is distinguished from the amplified DNA not carrying said polymorphism by restriction fragment polymorphism analysis.

7. The method according to claim 6, wherein restriction fragments are obtained by digestion of said amplified DNA with a restriction enzyme followed by migration in agarose gel followed by Southern blotting onto a membrane and hybridization.

* * * * *

SEQUENCE LISTING

<160> NUMBER OF SEQ ID NOS: 9

<210> SEQ ID NO 1
<211> LENGTH: 562
<212> TYPE: DNA
<213> ORGANISM: Homo sapiens

<400> SEQUENCE: 1

```
ttcatcacct gcgggtgggc caggggcttg gggcaggccc cggggaggac gccgcccctc      60
cctgccagcc cgcgcctcca gggagagtcc cggcccgcgc acctccttga gccggtgctc     120
cttctccgcc acgatgtgct ggatggtcat ggccacggag tagacccagg agatcaccat     180
gcacagcggc atcatgtgct caatgacaaa caggaagctg cggggaggcc gcgctcaggc     240
gccactcagc cccagcccca gcccagccc cgggcgccca gcactcactc atcgcgtgtg     300
tagcaggggt aggggaacat ctgcacgtag ctgcctggct ccaccacatc gtgccccaca     360
aaagtgtcga tgatggcgcg ctccatcatg tctgtgggtg ggggcagcca tcaggtgccg     420
ggcaggcccct ctcgtcctca cacctgtcct ccccatgaa tcctccagcc ggtcttccgg     480
gcctgctcct caccctggat ccagacgaag ccgtagagga agtagaagcg gccgccagta     540
ttgggcccag gccgccagta gg                                              562
```

<210> SEQ ID NO 2
<211> LENGTH: 562
<212> TYPE: DNA
<213> ORGANISM: Homo sapiens

<400> SEQUENCE: 2

```
ttcatcacct gcgggtgggc caggggcttg gggcaggccc cggggaggac gccgcccctc      60
cctgccagcc cgcgcctcca gggagagtcc cggcccgcgc acctccttga gccggtgctc     120
cttctccgcc acgatgtgct ggatggtcat ggccacggag tagacccagg agatcaccat     180
gcacagcggc atcatgtgct caatgacaaa caggaagctg cggggaggcc gcgctcaggc     240
gccactcagc cccagcccca gcccagccc cgggcgccca gcactcactc atcgcgtgtg     300
tagcaggggt aggggaacat ctgcacgtag ctgcctggct ccaccacgtc gtgccccaca     360
aaagtgtcga tggtggcgcg ctccatcatg tctgtgggtg ggggcagcca tcaggtgccg     420
ggcaggcccct ctcgtcctca cacctgtcct ccccatgaa tcctccagcc ggtcttccgg     480
gcctgctcct caccctggat ccagacgaag ccgtagagga agtagaagcg gccgccagta     540
ttgggcccag gccgccagta gg                                              562
```

<210> SEQ ID NO 3
<211> LENGTH: 400
<212> TYPE: DNA
<213> ORGANISM: Homo sapiens

<400> SEQUENCE: 3

```
gggcccaata ctggcggccg cttctacttc ctctacggct tcgtctggat ccagggtgag      60
gagcaggccc ggaagaccgg ctggaggatt catgggggag acaggtgtg aggacgagag      120 ggcctgcccg gcacctgatg gctgccccca cccacagaca tgatggagcg cgccatcatc     180 gacactttg tggggcacga tgtggtggag ccaggcagct acgtgcagat gttcccctac      240
ccctgctaca cacgcgatga gtgagtgctg ggcgcccggg gctggggctg ggctggggc      300 tgagtggcgc ctgagcgcgg cctccccgca gcttcctgtt tgtcattgag cacatgatgc     360
cgctgtgcat ggtgatctcc tgggtctact ccgtggccat                           400
```

<210> SEQ ID NO 4
<211> LENGTH: 400
<212> TYPE: DNA
<213> ORGANISM: Homo sapiens

<400> SEQUENCE: 4

```
gggcccaata ctggcggccg cttctacttc ctctacggct tcgtctggat ccagggtgag      60
gagcaggccc ggaagaccgg ctggaggatt catgggggag acaggtgtg aggacgagag      120 ggcctgcccg gcacctgatg gctgccccca cccacagaca tgatggagcg cgccatcatc     180 gacactttg tggggcacga cgtggtggag ccaggcagct acgtgcagat gttcccctac      240
ccctgctaca cacgcgatga gtgagtgctg ggcgcccggg gctggggctg ggctggggc      300 tgagtggcgc ctgagcgcgg cctccccgca gcttcctgtt tgtcattgag cacatgatgc     360
cgctgtgcat ggtgatctcc tgggtctact ccgtggccat                           400
```

<210> SEQ ID NO 5
<211> LENGTH: 8154
<212> TYPE: DNA
<213> ORGANISM: Homo sapiens

<400> SEQUENCE: 5

```
ggggcggagc cagcgcggat cgggtcccgg acgcccgagc gccccgcccc cgcgcgggcg      60
atgcccagcg gcgcggcggg ctgcggggcc cggcggggcg cgcagaggag cgggccgcgg     120
cgctgaggcg gcggagcgtg gccccgccat gggcttcctg caccagctgc agctgctgct     180
ctggaagaac gtgacgctca acgccggag ccgtgggtc ctggccttcg agatcttcat       240 cccccctggtg ctgttcttta tcctgctggg gctgcgacag aagaagccca ccatctccgt    300
gaaggaagtc cccttctaca cagcggcgcc cctgacgtct gccggcatcc tgcctgtcat    360
gcaatcgctg tgcccggacg gccagcgaga cgagttcggc ttcctgcagt acgccaactc    420
cacggtcacg cagctgcttg agcgcctgga ccgcgtggtg gaggaaggca acctgtttga    480
cccagcgcgg cccagcctgg gctcagagct cgaggcccta cgccagcatc tggaggccct    540
cagtgcgggc ccgggcacct cggggagcca cctggacaga tccacagtgt cttccttctc    600
tctggactcg gtgccagaa acccgcagga gctctggcgt ttcctgacgc aaaacttgtc    660
gctgcccaat agcacggccc aagcactctt ggccgcccgt gtggaccgc ccgaggtcta     720 ccacctgctc tttggtccct catctgccct ggattcacag tctggcctcc acaagggtca    780
ggagccctgg agccgcctag ggggcaatcc cctgttccgg atggaggagc tgctgctggc    840
tcctgccctc ctggagcagc tcacctgcac gccgggctcg ggggagctgg gccgatcct    900 cactgtgcct gagagtcaga agggagccct gcagggctac cgggatgctg tctgcagtgg    960
gcaggctgct gcgcgtgcca ggcgcttctc tgggctgtct gctgagctcc ggaaccagct   1020
ggacgtggcc aaggtctccc agcagctggg cctggatgcc cccaacggct cggactcctc   1080
```

-continued

```
gccacaggcg ccaccccac ggaggctgca ggcgcttctg ggggacctgc tggatgccca    1140
gaaggttctg caggatgtgg atgtcctgtc ggccctggcc ctgctactgc cccagggtgc    1200
ctgcactggc cggaccccg gaccccagc cagtggtgcg ggtggggcgg ccaatggcac    1260
tggggcaggg gcagtcatgg gccccaacgc caccgctgag gagggcgcac cctctgctgc    1320
agcactggcc accccggaca cgctgcaggg ccagtgctca gccttcgtac agctctgggc    1380
cggcctgcag cccatcttgt gtggcaacaa ccgcaccatt gaacccgagg cgctgcggcg    1440
gggcaacatg agctccctgg gcttcacgag caaggagcag cggaacctgg gcctcctcgt    1500
gcacctcatg accagcaacc ccaaaatcct gtacgcgcct gcgggctctg aggtcgaccg    1560
cgtcatcctc aaggccaacg agacttttgc ttttgtgggc aacgtgactc actatgccca    1620
ggtctggctc aacatctcgg cggagatccg cagcttcctg gagcagggca ggctgcagca    1680
acacctgcgc tggctgcagc agtatgtagc agagctgcgg ctgcaccccg aggcactgaa    1740
cctgtcactg gatgagctgc cgccggccct gagacaggac aacttctcgc tgcccagtgg    1800
catggccctc ctgcagcagc tggataccat tgacaacgcg cctgcggct ggatccagtt    1860
catgtccaag gtgagcgtgg acatcttcaa gggcttcccc gacgaggaga gcattgtcaa    1920
ctacaccctc aaccaggcct accaggacaa cgtcactgtt tttgccagtg tgatcttcca    1980
gacccggaag gacggctcgc tcccgcctca cgtgcactac aagatccgcc agaactccag    2040
cttcaccgag aaaaccaacg agatccgccg cgcctactgg cggcctgggc ccaatactgg    2100
cggccgcttc tacttcctct acggcttcgt ctggatccag gacatgatgg agcgcgccat    2160
catcgacact tttgtggggc acgacgtggt ggagccaggc agctacgtgc agatgttccc    2220
ctaccctgc tacacacgcg atgacttcct gtttgtcatt gagcacatga tgccgctgtg    2280
catggtgatc tcctgggtct actccgtggc catgaccatc cagcacatcg tggcggagaa    2340
ggagcaccgg ctcaaggagg tgatgaagac catgggcctg aacaacgcgg tgcactgggt    2400
ggcctggttc atcaccggct ttgtgcagct gtccatctcc gtgacagcac tcaccgccat    2460
cctgaagtac ggccaggtgc ttatgcacag ccacgtggtc atcatctggc tcttcctggc    2520
agtctacgcg gtggccacca tcatgttctg cttcctggtg tctgtgctgt actccaaggc    2580
caagctggcc tcggcctgcg gtggcatcat ctacttcctg agctacgtgc cctacatgta    2640
cgtggcgatc cgagaggagg tggcgcatga taagatcacg gccttcgaga gtgcatcgc    2700
gtccctcatg tccacgacgg cctttggtct gggctctaag tacttcgcgc tgtatgaggt    2760
ggccggcgtg ggcatccagt ggcacacctt cagccagtcc ccggtggagg gggacgactt    2820
caacttgctc ctggctgtca ccatgctgat ggtggacgcc gtggtctatg gcatcctcac    2880
gtggtacatt gaggctgtgc acccaggcat gtacggctg ccccggccct ggtacttccc    2940
actgcagaag tcctactggc tgggcagtgg gcggacagaa gcctgggagt ggagctggcc    3000
gtgggcacgc acccccgcc tcagtgtcat ggaggaggac caggcctgtg ccatggagag    3060
ccggcgcttt gaggagaccc gtggcatgga ggaggagccc acccaccagc ctctggttgt    3120
ctgcgtggac aaactcacca aggtctacaa ggacgacaag aagctggccc tgaacaagct    3180
gagcctgaac ctctacgaga accaggtggt ctccttcttg ggccacaacg gggcgggcaa    3240
gaccaccacc atgtccatcc tgaccggcct gttccctcca cgtcgggtt ccgccaccat    3300
ctacgggcac gacatccgca cggagatgga tgagatccgc aagaacctgg gcatgtgccc    3360
gcagcacaat gtgctctttg accggctcac ggtggaggaa cacctctggt tctactcacg    3420
```

```
gctcaagagc atggctcagg aggagatccg cagagagatg gacaagatga tcgaggacct    3480
ggagctctcc aacaaacggc actcactggt gcagacattg tcgggtggca tgaagcgcaa    3540
gctgtccgtg gccatcgcct tcgtgggcgg ctctcgcgcc atcatcctgg acgagcccac    3600
ggcgggcgtg gacccctacg cgcgccgcgc catctgggac ctcatcctga agtacaagcc    3660
aggccgcacc atccttctgt ccacccacca catggatgag gctgacctgc ttggggaccg    3720
cattgccatc atctcccatg ggaagctcaa gtgctgcggc tccccgctct tcctcaaggg    3780
cacctatggc gacgggtacc gcctcacgct ggtcaagcgg cccgccgagc cgggggggccc    3840 ccaagagcca gggctggcat ccagcccccc aggtcgggcc ccgctgagca gctgctccga    3900
gctccaggtg tcccagttca tccgcaagca tgtggcctcc tgcctgctgg tctcagacac    3960
aagcacggag ctctcctaca tcctgcccag cgaggccgcc aagaagggggg ctttcgagcg    4020 cctcttccag cacctggagc gcagcctgga tgcactgcac ctcagcagct tcgggctgat    4080
ggacacgacc ctggaggaag tgttcctcaa ggtgtcggag gaggatcagt cgctggagaa    4140
cagtgaggcc gatgtgaagg agtccaggaa ggatgtgctc cctggggcgg agggcccggc    4200
gtctggggag ggtcacgctg gcaatctggc ccggtgctcg gagctgaccc agtcgcaggc    4260
atcgctgcag tcggcgtcat ctgtgggctc tgcccgtggc gacgagggag ctggctacac    4320
cgacgtctat ggcgactacc gccccctctt tgataaccca caggaccag acaatgtcag    4380 cctgcaagag gtggaggcag aggccctgtc gagggtcggc cagggcagcc gcaagctgga    4440
cggcgggtgg ctgaaggtgc gccagttcca cgggctgctg gtcaaacgct tccactgcgc    4500
ccgccgcaac tccaaggcac tcttctccca gatcttgctg ccagccttct tcgtctgcgt    4560
ggccatgacc gtggccctgt ccgtcccgga gattggtgat ctgcccccgc tggtcctgtc    4620
accttcccag taccacaact acacccagcc ccgtggcaat ttcatcccct acgccaacga    4680
ggagcgccgc gagtaccggc tgcggctatc gcccgacgcc agcccccagc agctcgtgag    4740
cacgttccgg ctgccgtcgg gggtgggtgc cacctgcgtg ctcaagtctc ccgccaacgg    4800
ctcgctgggg cccacgttga acctgagcag cggggagtcg cgcctgctgg cggctcggtt    4860
cttcgacagc atgtgtctgg agtccttcac acagggggctg ccactgtcca atttcgtgcc    4920
acccccaccc tcgcccgccc catctgactc gccagcgtcc ccggatgagg acctgcaggc    4980
ctggaacgtc tccctgccgc ccaccgctgg gccagaaatg tggacgtcgg caccctccct    5040
gccgcgcctg gtacgggagc ccgtccgctg cacctgctct gcgcagggca ccggcttctc    5100
ctgccccagc agtgtgggcg ggcacccgcc ccagatgcgg gtggtcacag gcgacatcct    5160
gaccgacatc accggccaca atgtctctga gtacctgctc ttcacctccg accgcttccg    5220
actgcaccgg tatggggcca tcacctttgg aaacgtcctg aagtccatcc cagcctcatt    5280
tggcaccagg gccccaccca tggtgcggaa gatcgcggtg cgcagggctg cccaggtttt    5340
ctacaacaac aagggctatc acagcatgcc cacctacctc aacagcctca caacgccat    5400 cctgcgtgcc aacctgccca gagcaagggg caacccggcg gcttacggca tcaccgtcac    5460
caaccacccc atgaataaga ccagcgccag cctctccctg gattacctgc tgcagggcac    5520
ggatgtcgtc atcgccatct tcatcatcgt ggccatgtcc ttcgtgccgg ccagcttcgt    5580
tgtcttcctc gtgccagaga gtccaccaa ggccaagcat ctgcagtttg tcagcggctg    5640
caaccccatc atctactggc tggcgaacta cgtgtgggac atgctcaact acctggtccc    5700
cgctacctgc tgtgtcatca tcctgtttgt gttcgacctg ccggcctaca cgtcgcccac    5760
caacttccct gccgtcctct ccctcttcct gctctatggg tggtccatca cgcccatcat    5820
```

```
gtacccggcc tccttctggt tcgaggtccc cagctccgcc tacgtgttcc tcattgtcat   5880
caatctcttc atcggcatca ccgccaccgt ggccaccttc ctgctacagc tcttcgagca   5940
cgacaaggac ctgaaggttg tcaacagtta cctgaaaagc tgcttcctca ttttccccaa   6000
ctacaacctg gccacgggc tcatggagat ggcctacaac gagtacatca acgagtacta   6060
cgccaagatt ggccagtttg acaagatgaa gtcccgtc gagtgggaca ttgtcacccg   6120
cggactggtg gccatggcgg ttgagggcgt cgtgggcttc ctcctgacca tcatgtgcca   6180
gtacaacttc ctgcggcggc cacagcgcat gcctgtgtct accaagcctg tggaggatga   6240
tgtggacgtg gccagtgagc ggcagcgagt gctccgggga gacgccgaca atgacatggt   6300
caagattgag aacctgacca aggtctacaa gtcccggaag attggccgta tcctggccgt   6360
tgaccgcctg tgcctgggtg tgcgtcctgg cgagtgcttc gggctcctgg gcgtcaacgg   6420
tgcgggcaag accagcacct tcaagatgct gaccggcgac gagagcacga cggggggcga   6480
ggccttcgtc aatggacaca gcgtgctgaa ggagctgctc caggtgcagc agagcctcgg   6540
ctactgcccg cagtgtgacg cgctgttcga cgagctcacg gcccgggagc acctgcagct   6600
gtacacgcgg ctgcgtggga tctcctggaa ggacgaggcc cgggtggtga agtgggctct   6660
ggagaagctg gagctgacca agtacgcaga caagccggct ggcacctaca gcggcggcaa   6720
caagcggaag ctctccacgg ccatcgccct cattgggtac ccagccttca tcttcctgga   6780
cgagcccacc acaggcatgg accccaaggc ccggcgcttc ctctggaacc tcatcctcga   6840
cctcatcaag acagggcgtt cagtggtgct gacatcacac agcatggagg agtgcgaggc   6900
gctgtgcacg cggctggcca tcatggtgaa cggtcgcctg cggtgcctgg cagcatcca   6960
gcacctgaag aaccggtttg agatggcta catgatcacg gtgcggacca agagcagcca   7020
gagtgtgaag gacgtggtgc ggttcttcaa ccgcaacttc ccggaagcca tgctcaagga   7080
gcggcaccac acaaaggtgc agtaccagct caagtcggag cacatctcgc tggcccaggt   7140
gttcagcaag atggagcagg tgtctggcgt gctgggcatc gaggactact cggtcagcca   7200
gaccacactg gacaatgtgt tcgtgaactt tgccaagaag cagagtgaca acctggagca   7260
gcaggagacg gagccgccat ccgcactgca gtcccctctc ggctgcttgc tcagcctgct   7320
ccggccccgg tctgccccca cggagctccg ggcacttgtg gcagacgagc ccgaggacct   7380
ggacacggag gacgagggcc tcatcagctt cgaggaggag cgggcccagc tgtccttcaa   7440
cacgacacg ctctgctgac cacccagagc tgggccaggg aggacacgct ccactgacca   7500
cccagagctg ggccagggac tcaacaatgg ggacagaagt cccccagtgc ctgccagggc   7560
ctggagtgga ggttcaggac caaggggctt ctggtcctcc agcccctgta ctcggccatg   7620
ccctgcggtc actgcggttg ccgcccctaa ttgtgccaaa ggctgacccg cccgggctg   7680
cgtacaccct tgccctgctt tgccttaaag cctcggggtc tgcccggccc ctcgcccctg   7740
cctggcactg ctcaccgccc aaggcgacgc cggctggacc aggcactgct ggcctttctc   7800
ctgcccggcc tcggaaccag cttttctctc ttacgatgaa ggctgatgcc gagagcgggc   7860
tgtgggcgga gctgggtcag tcccgtattt atttttgcttt gagaagaggc tcctctggcc   7920
ctgctctcct gcaggggagt ggctgtcccg cgggaagcca tcagcttggg ccagctggca   7980
ggtggcagga atggagaagc tgaccctgct ggccaggcaa ggggccagac ccccccaac   8040
ccccagctgc catcgctctc ccacccagct tggcccctg cccgcccacc tccctgggag   8100
ccgggcctgt acatagcgca cagatgtttg ttttaaataa ataaacaaaa tgtc          8154
```

```
<210> SEQ ID NO 6
<211> LENGTH: 16
<212> TYPE: DNA
<213> ORGANISM: Homo sapiens

<400> SEQUENCE: 6
agcgcgccat catcga                                                    16

<210> SEQ ID NO 7
<211> LENGTH: 20
<212> TYPE: DNA
<213> ORGANISM: Homo sapiens

<400> SEQUENCE: 7
cactcatcgc gtgtgtagca                                                20

<210> SEQ ID NO 8
<211> LENGTH: 15
<212> TYPE: DNA
<213> ORGANISM: Homo sapiens

<400> SEQUENCE: 8
cacgatgtgg tggag                                                     15

<210> SEQ ID NO 9
<211> LENGTH: 14
<212> TYPE: DNA
<213> ORGANISM: Homo sapiens

<400> SEQUENCE: 9
cacgacgtgg tgga                                                      14
```